US006903124B2

(12) United States Patent
Cho et al.

(10) Patent No.: US 6,903,124 B2
(45) Date of Patent: Jun. 7, 2005

(54) ORGANIC ACID SALT OF AMLODIPINE

(75) Inventors: Seong Hwan Cho, Suwon-si (KR);
Yong Sik Youn, Yongin-si (KR); Yun Taek Jung, Seoul (KR); Choong Sil Park, Icheon-si (KR); Hyuk Koo Lee, Yongin-si (KR); Kwang Hyeg Lee, Seongnam-si (KR); Eun Ju Jeong, Chungcheongbuk-do (KR); Young Hoon Kim, Seoul (KR); Hae Tak Jin, Yongin-si (KR); Jun Hee Cheon, Suwon-si (KR); Sung Hak Lee, Yongin-si (KR); Sung Hak Jung, Seoul (KR); Dong Kwon Lim, Seongnam-si (KR); Kyu Jeong Yeon, Yongin-si (KR); Yun Cheul Kim, Seoul (KR); Kyung Mi Park, Seoul (KR); Hyun Suk Kang, Seoul (KR)

(73) Assignee: CJ Corp, Seoul (KR)

( * ) Notice: Subject to any disclaimer, the term of this patent is extended or adjusted under 35 U.S.C. 154(b) by 68 days.

(21) Appl. No.: 10/628,268

(22) Filed: Jul. 29, 2003

(65) Prior Publication Data

US 2004/0029931 A1 Feb. 12, 2004

(30) Foreign Application Priority Data

Jul. 30, 2002 (KR) .................................. 10-2002-0044858

(51) Int. Cl.[7] ........................ A61K 31/44; C07D 213/80
(52) U.S. Cl. ....................................... 514/356; 546/321
(58) Field of Search ........................... 514/356; 546/321

(56) References Cited

U.S. PATENT DOCUMENTS

| 4,572,909 A | 2/1986 | Campbell et al. |
| 4,758,569 A | 7/1988 | Swindell |
| 4,806,557 A | 2/1989 | Campbell et al. |
| 4,879,303 A | 11/1989 | Davison et al. |
| 6,057,344 A | 5/2000 | Young |
| 6,291,490 B1 | 9/2001 | Young |
| 6,756,390 B2 | 6/2004 | Cho et al. |
| 2002/0086888 A1 | 7/2002 | Benneker et al. |

FOREIGN PATENT DOCUMENTS

| EP | 0089167 | 9/1983 |
| EP | 0244944 | 3/1987 |
| KR | 95-7228 | 4/1989 |
| KR | 19912145 | 4/1989 |
| KR | 2002-0076561 | 10/2002 |
| WO | 99/52873 | 10/1999 |
| WO | 02/053538 | 7/2002 |

OTHER PUBLICATIONS

English Language Abstract of KR 2002–0076561, published Oct. 11, 2002.

*Primary Examiner*—Patricia L. Morris
(74) *Attorney, Agent, or Firm*—Greenblum & Bernstein, P.L.C.

(57) ABSTRACT

Disclosed are a novel organic acid salt of amlodipine, its preparation method, and a pharmaceutical composition containing as a therapeutically active ingredient the same.

9 Claims, No Drawings

ORGANIC ACID SALT OF AMLODIPINE

BACKGROUND OF THE INVENTION

1. Field of the Invention

The present invention relates to a novel organic acid salt of amlodipine (2-[(2-aminoethoxy)methyl]-4-(2-chlorophenyl)-1,4-dihydro-6-methyl-3,5-pyridinedicarboxylic acid 3-ethyl 5-methyl ester), represented by the following formula 1, its preparation method, and a pharmaceutical composition containing the same as an effective ingredient.

[Chemical Formula 1]

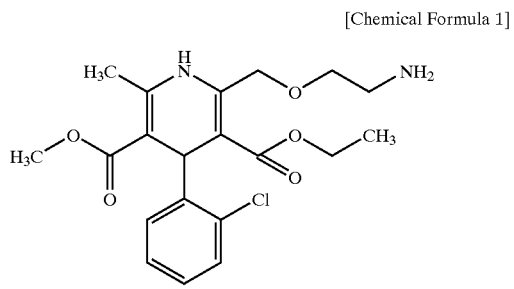

2. Description of the Prior Art

With activity to block calcium channels in the body, amlodipine is used for the treatment of hypertension. This calcium channel blocker is found in many prior arts.

European Pat. Laid-Open Publication No. 89,167 discloses acid salts of amlodipine which can be formed from acids which may form nontoxic acid addition salts with pharmaceutically acceptable anions, such as hydrochloride, hydrobromide, sulfate, phosphate, acetate, maleate, fumarate, lactate, tartrate, citrate, gluconate, etc.

U.S. Pat. No. 6,291,490 introduces a pharmaceutical composition containing as an active ingredient S-(-)-amlodipine which possesses potent activity in treating hypertension without adverse effects associated with the administration of the racemic mixture of amlodipine.

Both U.S. Pat. No. 4,879,303 and Korean Pat. Laid-Open Publication No. 1989-3375 disclose amlodipine besylate, saying that amlodipine besylate is superior to other salts of amlodipine, such as hydrochloride, acetate and mesylate in physicochemical properties including (1) solubility, (2) stability, (3) non-hygroscopicity, and (4) processability for tablet formulation.

However, since amlodipine besylate in current use is relatively low in solubility at pH 1–7.4, there is a need for novel salts which are of sufficient solubility, so as to increase the bioavailability of amlodipine and easily formulate its injections. Additionally, amlodipine besylate has been found to be sensitive to light. Therefore lysates are generated when the salt is exposed to light.

Further, amlodipine besylate is disadvantageous due to benzene sulfonic acid being used in its production process. That is, benzene sulfonic acid is difficult to industrially treat because it is corrosive and toxic. In addition, its high hygroscopicity requires special procedures for transport, delivery and use. Another disadvantage is that the water content of benzene sulfonic is too high, amounting to about 10%. In order to avoid these problems, ammonium benzene sulfonate is employed as an alternative, but with the concomitant generation of ammonia gas. This method needs additional processes for absorbing and inactivating ammonia gas (PCT Publication No. WO1999/52873).

DISCLOSURE OF THE INVENTION

Leading to the present invention, the intensive and thorough research into therapeutically effective organic acid salts of amlodipine, conducted by the present inventors aiming to overcome the problems encountered in prior arts, resulted in the finding that amlodipine ethanesulfonate has excellent physicochemical properties including solubility, non-hygroscopicity, chemical and light stability, and processability for dosage formation so that the amlodipine ethanesulfonate is industrially and medically useful.

Therefore, it is an object of the present invention to provide an ethanesulfonic acid salt of amlodipine.

It is another object of the present invention to provide a method for preparing an ethanesulfonic acid salt of amlodipine.

It is a further object of the present invention to provide a pharmaceutical composition containing the ethanesulfonic acid salt of amlodipine as a therapeutically active ingredient.

In accordance with an aspect of the present invention, there is provided an ethanesulfonic acid salt of amlodipine and preferably a crystalline ethanesulfonic acid salt of amlodipine.

In accordance with another aspect of the present invention, there is provided a method for preparing an ethanesulfonate acid salt of amlodipine, in which ethanesulfonic acid is reacted with amlodipine in an inert solvent.

In accordance with a further aspect of the present invention, there is provided a pharmaceutical composition effective for the treatment of ischemic cardiac disorders or hypertension, comprising a therapeutically effective amount of amlodipine ethanesulfonate and a pharmaceutically acceptable diluent or carrier preferably in the dosage form of tablets, capsules, solutions or injectables.

DETAILED DESCRIPTION OF THE INVENTION

The present invention encompasses amlodipine ethansulfonate, represented by the following chemical formula 2.

[Chemical Formula 2]

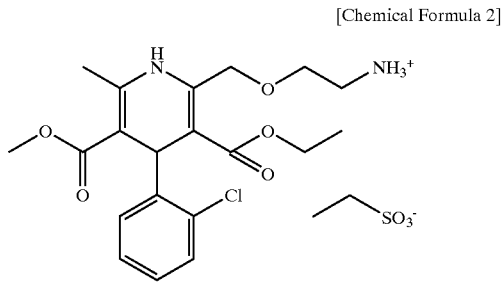

Compared to amlodipine besylate in a commercially acceptable form, amlodipine ethanesulfonate exhibits equal or better non-hygroscopicity, formulation processability and chemical stability and especially, at least 200 times greater solubility in distilled water or in various pH conditions. Accordingly, with the feasibility of being formulated into dosage forms such as liquids and injections as well as the difficulty of being precipitated in blood, the amlodipine ethansulfonate of the present invention is of great bioavailability.

Ethanesulfonic acid salts of amlodipine according to the present invention may be in a crystal form or an amorphous form with preference to a crystal form.

The present invention also encompasses a method for preparing ethanesulfonic acid salts of amlodipine. The salts can be prepared by reacting amlodipine with ethanesulfonic acid in an inert solvent, as illustrated in the following reaction formula 1.

[Reaction Formula 1]

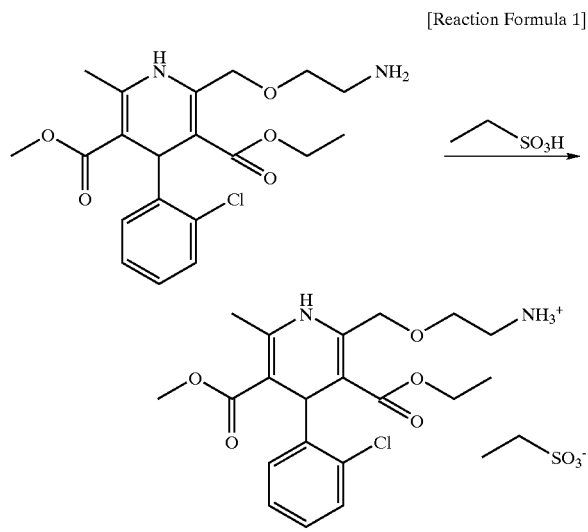

Ethanesulfonic acid, a stable, colorless chemical with FDA permission for use in pharmaceuticals, is in a liquid state at room temperature and shows neither hygroscopicity nor corrosiveness nor toxicity. With these properties, ethanesulfonic acid is easily handled and can be safe enough for production of amlodipine ethanesulfonate in a mass scale.

Examples of the inert solvent suitable for the preparation of the salt of the present invention include ethyl acetate, methanol, ethanol, isopropanol, acetonitrile, hexane, isopropyl ether and etc. with preference to methanol.

In the inert solvent, ethanesulfonic acid is used in the amount of 1–2 equivalents and preferably in the amount of 1.02–1.2 equivalents per equivalent of amlodipne. The reaction is performed at −5 to 30° C. and preferably at 0 to 15° C. for 0.5 to 5 hours and preferably for 1 to 3 hours.

According to the method of the present invention, amlodipine ethanesulfonate can be prepared at a yield of 90% or higher.

Also, the present invention encompasses a pharmaceutical composition useful in the treatment of ischemic cardiac disorders or hypertension, which comprises a therapeutically effective amount of amlodipine ethanesulfonate and a pharmaceutically acceptable diluent or carrier.

The composition of the present invention may be formulated into oral dosage forms including, but not limited to, granules, powders, solutions, tablets, capsules, dry syrup and the like, or parenteral dosage forms including injectables. The composition of the present invention is preferably in the dosage form of tablets, capsules, solutions or injectables.

To be therapeutically effective, amlodipine ethanesulfonate is administered in the amount of 2–10 mg per day on the basis of the weight of amlodipine. In a unit dosage form, amlodipine ethanesulfonate is contained in the amount of 2.5–12.8 mg.

In practical use, amlodipine ethanesulfonate can be combined as the active ingredient in intimate admixture with a pharmaceutically acceptable diluent or carrier selected from among excipients, disintegrants, binders and lubricants, and mixtures thereof. The carrier may take a wide variety of forms depending on the form of the preparation desired for administration. In preparing the composition in a solid dosage form such as a tablet or a hard capsule, there may be employed microcrystalline cellulose, lactose, low-substituted hydroxycellulose and the like as an excipient; sodium starch glycollate, anhydrous monohydrogenphosphate and the like as a disintegrant; polyvinylpyrrolidone, low-substituted hydroxypropylcellulose, hydroxypropylcellulose and the like as a binder; and magnesium stearate, silica, talc and the like as a lubricant.

A formulation may comprise an additive to provide sheen to the tablet such as anhydrous dibasic calcium phosphate. To prevent atmospheric moisture of air from penetrating into the tablet, it may have a water-insoluble coating. The coating base must have a dense molecular structure and preferably, low solubility in water. Suitable for the base is a polymeric material selected from among methacrylic acid copolymer, hydroxypropylmethyl cellulose phthalate, cellulose acetate phthalate, hydroypropylmethylcellulose acetate succinate, polyvinyl alcohol and combinations thereof. Also, the coating may comprise conventional additives such as plasticizers, preservatives, coloring agents, light shielders, etc.

The composition of the present invention may be in the form of solutions such as sterile aqueous solution, or injectables. Such solution contains, if necessary, from 10 to 40% of propylene glycol and sodium chloride sufficient to avoid hemolysis (e.g. about 1%).

A better understanding of the present invention may be obtained in light of the following examples which are set forth to illustrate, but are not to be construed to limit the present invention.

EXAMPLES

Amlodipine ethanesulfonate prepared according to the present invention was tested for various physical properties. First, the salt was formulated into tablets, capsules and aqueous solutions to test for the processability for dosage formation. Also, amlodipine ethanesulfonate was compared with amlodipine besylate with regard to hydroscopicity, solubility, stability and light stability.

In the following reference examples, the starting material and conventional salts of amlodipine were prepared according to methods disclosed in the art.

Reference Example 1
Preparation of Amlodipine Besylate

Amlodipine was prepared as disclosed in Korean Pat. Publication No. 87-809. The method described in Korean Pat. Publication No. 95-7228 was adopted to produce amlodipine besylate.

Example 1
Preparation of Amlodipine Ethanesulfonate

Into a 1L three-neck flask, ethanesulfonic acid (11.56 g, 1.05 equivalents) and methanol (200 ml) were poured. To the flask, a solution of amlodipine (40.8 g, 0.1 mole) in methanol (300 ml) was added dropwise. The resulting solution was stirred at 23° C. for 2 hours, cooled to 7° C. and stirred again for 1 hour to produce precipitates. They were washed at 5° C. with methanol (100 ml) and n-hexane (100 ml), filtered, and dried at 35° C. in vacuo to afford 46.4 g of amlodipine ethanesulfonate as a white crystalline solid (Yield 90%).

The element analysis and melting point of the amlodipine ethanesulfonate prepared above were determined.

TABLE 1

| Element analysis for $C_{22}H_{31}ClN_2O_8S$ (%) | | | | | |
|---|---|---|---|---|---|
| Found | C: 50.9 | H: 6.0 | N: 5.4 | S: 6.2 | O: 22.4 |
| Calculated | C: 50.8 | H: 6.0 | N: 5.3 | S: 6.3 | O: 24.7 |

Melting point: 190° C.
(measured by capillary melting point method with heating rate of about 1° C./minute)

Example 2

Formulation of Tablet Containing Amlodipine Ethanesulfonate

The ingredients given in Table 2 were formulated to prepare a tablet containing amlodipine ethanesulfonate.

TABLE 2

| Ingredients | Contents (mg per tablet) |
|---|---|
| Amlodipine ethanesulfonate | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press from Jowoon Machinery, and the compressed material was formulated into tablets using a tableting machine from Erweka.

Example 3

Formulation of Tablet Containing Amlodipine Ethanesulfonate

The ingredients given in Table 3 were blended and formulated into tablets containing amlodipine ethanesulfonate.

TABLE 3

| Ingredients | Contents (mg per tablet) |
|---|---|
| Amlodipine ethanesulfonate | 5.0 based on Amlodipine |
| Lactose | 180 |
| Cross Povidone | 6 |
| Polyvinylpyrrolidone K90 | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and formulated into tablets using a tableting machine from Erweka.

Example 4

Formulation of Capsule Containing Amlodipine Ethanesulfonate

The ingredients given in Table 4 were formulated to prepare a capsule containing amlodipine ethanesulfonate.

TABLE 4

| Ingredients | Contents (mg per capsule) |
|---|---|
| Amlodipine ethanesulfonate | 5.0 based on Amlodipine |
| Low-substituted Hydroxypropylcellulose | 65 |
| Microcrystalline Cellulose | 120 |
| Sodium Starch Glycollate | 4 |
| Magnesium Stearate | 2 |

The ingredients were blended and the blend was compressed using a roller press from Jowoon Machinery, and then the compressed material was filled into hard gelatin capsules using a capsule filling device from Bosche.

Example 5

Formulation of Capsule Containing Amlodipine Ethanesulfonate

The ingredients given in Table 5 were formulated to prepare a capsule containing amlodipine ethanesulfonate.

TABLE 5

| Ingredients | Contents (mg per capsule) |
|---|---|
| Amlodipine ethanesulfonate | 5.0 based on Amlodipine |
| Lactose | 180 |
| Cross Povidone | 6 |
| Polyvinylpyrrolidone K90 | 6 |
| Sodium Starch Glycollate | 4 |
| Magnesium Stearate | 2 |

Lactose, cross povidone and polyvinylpyrrolidone K90 were preblended. The pre-blend was granulated according to a fluidized bed assembly method (SPIRA FLOW) and the granules were blended with the remaining ingredients and filled in hard gelatin capsules using a capsule filling device from Bosche.

Example 6

Test for Hygroscopicity of Amlodipine Ethanesulfonate

Amlodipine ethanesulfonate prepared in Example 1 and amlodipine besylate prepared in Reference Example 1 were tested for hygroscopicity by measuring their water contents (K. F. water %) at 25° C. under various humidity conditions. The results are given in Table 6, below.

TABLE 6

| Humidity Conditions (RH) | | 25% | 60% | 75% | 95% |
|---|---|---|---|---|---|
| Storage Period (week) | Initial | 1 | 1 | 1 | 1 |
| Ethanesulfonate (%) | 0.12 | 0.08 | 0.09 | 0.13 | 0.15 |
| Besylate (%) | 0.14 | 0.10 | 0.09 | 0.15 | 0.17 |

As shown in Table 6, the non-hydrogscopicity of amlodipine ethanesulfonate is equal to or better than that of amlodipine besylate. With a hygroscopicity of 0.5% or less at relative humidity 95%, the salt is suitable for the formulation of tablets, capsules, injectables, and the like.

Example 7

Test for Solubility of Amlodipine Ethanesulfonate

Solubilities of amlodipine ethanesulfonate prepared in Example 1 and amlodipine besylate prepared in Reference Example 1 in various solvents were measured at 37° C. The results are given in Table 7, below. The solubilities (mg/ml) of Table 6 are values based on the weight of amlodipine converted from the salts.

TABLE 7

| Solvents | Salts (mg/ml) | | Note |
|---|---|---|---|
| | Ethanesulfonate | Besylate | |
| Dist. water | >200 | 1.29 | Ionic Strength 0.2 buffer |
| pH 2 | >200 | 1.29 | Dissolved at 37° C. |
| pH 4 | >200 | 1.32 | |
| pH 6 | >200 | 1.28 | |
| pH 7 | >200 | 0.64 | |
| pH 7.4 | >200 | 1.35 | |
| pH 8 | >200 | 1.25 | |

As seen in Table 7, solubilities of amlodipine ethanesulfonate in distilled water and buffers of various pH are at least 200 times greater than those of amlodipine besylate. That is, amlodipine ethanesulfonate shows far superior solubility properties over amlodipine besylate.

Example 8
Test for Stability of Amlodipine Ethanesulfonate
1. Chemical Stability of Amoldipine Ethanesulfonate in Solid State Amlodipine ethanesulfonate prepared in Example 1 and amlodipine besylate prepared in Reference Example 1 were subjected to accelerated test at 60° C. and the results are summarized in Table 8, below.

TABLE 8

| Salts | Storage Period | | | |
|---|---|---|---|---|
| | initial | 1 week | 2 weeks | 3 weeks |
| Ethanesulfonate | 99.7% | 99.6% | 99.6% | 99.5% |
| Besylate | 99.6% | 99.6% | 99.4% | 99.2% |

(unit: HPLC content %)

HPLC Analysis Conditions:
Detector: UV Absorbance (at 237 nm)
Column: Octadesyl silica gel C18 (4.6 mm×150 mm, 5 μm)
Mobile Phase: Potassium dihydrogenphosphate monobasic (0.03M): methanol=4:6 (v/v)
Flow Rate: 1.5 ml/min As shown in Table 8, there were virtually no changes occurred in the content of amlodipine ethanesulfonate, like amlodipine besylate, as measured by accelerated test at 60° C. The data of Table 8 demonstrate that, comparable to that of amlodipine besylate, the chemical stability of amlodipine ethanesulfonate is excellent.

2. Chemical Stability of Amlodipine Ethanesulfonate in Aqueous State

To investigate stability in aqueous state, amlodipine ethanesulfonate prepared in Example 1 and amlodipine besylate prepared in Reference Example 1 were separately dissolved in distilled water. The resulting aqueous solutions were stored at 25° C. for 4 weeks in complete darkness, after which a measurement was made of the contents of the salts with resort to HPLC under the same conditions as in the solid state.

The results of the light-shielded stability test indicate that neither decomposition products nor content change is found in both amlodipine ethanesulfonate and amodipine besylate.

Taken together, the data observed in the above examples indicate that the amlodipine ethanesulfonate of the present invention has excellent physicochemical properties including non-hygroscopicity, chemical and optical stability, solubility and processability for dosage formulation and is easy to deliver in the body of a patient in addition to being stored for a long period of time. Further, free of the corrosiveness and toxicity, ethanesulfonic acid is industrially useful.

What is claimed is:

1. An ethanesulfonic acid salt of amlodipine.
2. The ethanesulfonic acid salt of amlodipine as defined in claim 1, wherein the salt is in crystalline form.
3. A method for preparing an ethanesulfonic acid salt of amlodipine, comprising the step of reacting amlodipine with ethanesulfonic acid in an inert solvent.
4. A pharmaceutical composition for the treatment of ischemic cardiac disorders or hypertension, comprising a therapeutically effective amount of the ethansulfonic acid salt of amlodipine of claim 1, and a pharmaceutically acceptable diluent or carrier.
5. The pharmaceutical composition as defined in claim 4, wherein the composition is in the form of tablets or capsules.
6. The pharmaceutical composition as defined in claim 4, wherein the composition is in the form of liquids or injectables.
7. A pharmaceutical composition for the treatment of ischemic cardiac disorders or hypertension, comprising a therapeutically effective amount of the ethanesulfonic acid salt of amlodipine of claim 2, and a pharmaceutically acceptable diluent or carrier.
8. The pharmaceutical composition as defined in claim 7, wherein the composition is in the form of tablets or capsules.
9. The pharmaceutical composition as defined in claim 7, wherein the composition is in the form of solutions or injectables.

* * * * *